United States Patent [19]
Mitchell et al.

[11] Patent Number: 5,817,797
[45] Date of Patent: Oct. 6, 1998

[54] SEQUENCING DNA; A MODIFICATION OF THE POLYMERASE CHAIN REACTION

[75] Inventors: Lloyd G. Mitchell, Bethesda; Carl R. Merril, Rockville, both of Md.

[73] Assignee: The United States of America as represented by the Department of Health and Human Services, Washington, D.C.

[21] Appl. No.: 200,876

[22] Filed: Jun. 1, 1988

[51] Int. Cl.⁶ .............................. C07H 21/00; C12Q 1/68; C12P 19/34
[52] U.S. Cl. .................... 536/25.3; 536/25.4; 536/25.41; 435/6; 435/91.1
[58] Field of Search ........................... 435/6, 172.3, 810, 435/91, 803, 17, 3; 536/26, 27, 28, 29, 25.3, 25.4

[56] References Cited

U.S. PATENT DOCUMENTS

| | | | |
|---|---|---|---|
| 4,683,202 | 7/1987 | Mullis | 435/6 |
| 4,729,947 | 3/1988 | Middendorf et al. | 435/6 |
| 4,766,062 | 8/1988 | Diamond et al. | 435/6 |
| 4,840,892 | 6/1989 | Adams et al. | 435/6 |
| 4,965,188 | 10/1990 | Mullis et al. | 435/6 |
| 4,988,617 | 1/1991 | Landegren et al. | 536/27 |
| 5,043,272 | 8/1991 | Hartley | 435/91 |
| 5,066,584 | 11/1991 | Gyllensten et al. | 435/6 |
| 5,273,879 | 12/1993 | Goodman et al. | 435/6 |
| 5,340,728 | 8/1994 | Grosz et al. | 435/91.2 |
| 5,405,746 | 4/1995 | Uhlen | 435/6 |
| 5,480,784 | 1/1996 | Kacian et al. | 435/91.21 |
| 5,518,900 | 5/1996 | Nikiforov et al. | 435/91.1 |

FOREIGN PATENT DOCUMENTS

| | | |
|---|---|---|
| 3844485 | 8/1985 | Australia . |
| 6236486 | 3/1987 | Australia . |
| 8009787 | 4/1988 | Australia . |
| 0063879 | 3/1982 | European Pat. Off. . |
| 063879 | 4/1982 | European Pat. Off. . |

OTHER PUBLICATIONS

NIO–Label Kits Clontech Laboratories Inc. (1989/1990).
Dynabeads M–280 Technical Handbook (c. 1989 by DYNAL).
Syvanen et al., Nucleic Acids Research, vol. 14, No. 12, pp. 5037–5048, (1986).
Cook et al., Nucleic Acid Research, vol. 16, No. 9, May 1988.
Delius et al., Nucleic Acid Research, vol. 13, No. 15, pp. 5457–5469 (1985).
Murasugi et al., DNA, vol. 3, No. 3, pp. 269–277, (1985).

*Primary Examiner*—James O. Wilson
*Attorney, Agent, or Firm*—Fitch, Even, Tabin & Flannery

[57] ABSTRACT

The invention provides a process wherein a biotinylated oligonucleotide primer and an oligonucleotide primer which has not undergone biotinylation are used when amplifying a DNA sequence to facilitate separation of the DNA strands following the polymerase chain reaction process. The biotinylation/PCR product is then exposed to a support which will selectively bind the biotinylated strand to allow selective elution of the product.

7 Claims, 6 Drawing Sheets

Fig. 1b

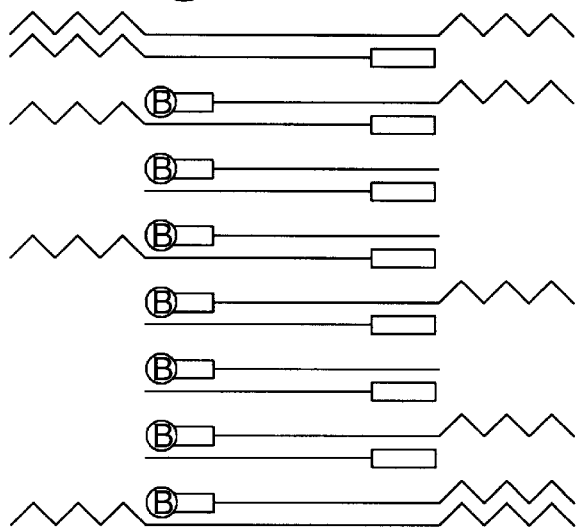

6) PRIMER EXTENSION

END OF ROUND 3:
2 COPIES LONG PRODUCT
3 COPYS SHORT PRODUCT

END OF ROUND 4:
4 COPIES LONG PRODUCT
10 COPIES SHORT PRODUCT

BIOTINYLATED SHORT PRODUCT
ACCUMULATES EXPONENTIALLY

BIOTINYLATED LONG PRODUCT
ACCUMULATES LINEARLY

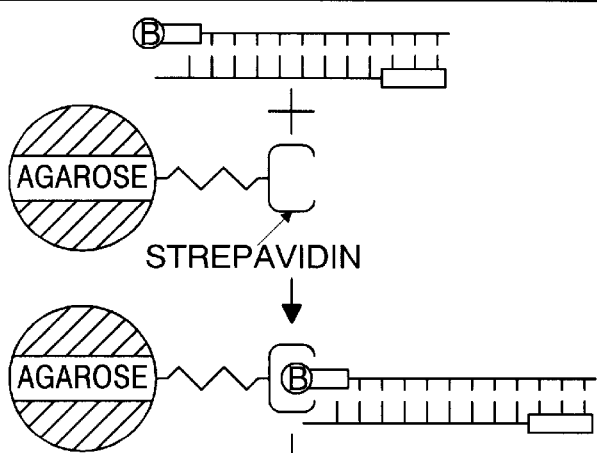

7) BIOTINYLATED SHORT
PRODUCT-
MAJOR REACTION PRODUCT

STREPAVIDIN AGAROSE

BIOTIN STREPAVIDIN
AGAROSE COMPLEX

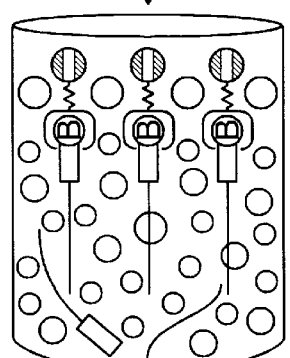

ADD COMPLEX TO
SEPHADEX COLUMN

DENATURE WITH NaOH

CENTRIFUGE COLUMN

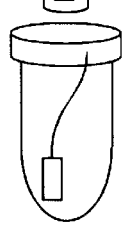

COLLECT SINGLE
STRAND DNA

BIOTINYLATED STRAND
REMAINS ON COLUMN

Fig. 4

| | 146 | 150 | 152 | 158 | 185 | 186 | 189 | 195 | 200 | @228 | 236 | 247 | @257 | 263 | @381 | @382 | NUCLEOTIDE POSITIONS SEQUENCED |
|---|---|---|---|---|---|---|---|---|---|---|---|---|---|---|---|---|---|
| ANDERSON | A | G | G | A | G | C | G | T | A | T | G | A | C | T | C | C | |
| pCJK | / | / | / | G | | | | | G | | | | | | | | 152-242/341-427 |
| pBHK | | | | | | | | | | | | | | / | | | 144-244/342-420 |
| pLKK | G | | | | G | | | | | | | | | / | | | 144-244/342-420 |
| pCDK | / | / | / | A | *T | G | | | | | | T | C | C | | | 172-294/329-440 |
| Mt 77374 | | | | | G | A | A | C | G | | | T | C | C | / | / | 142-294 |
| Mt 81368 | | | / | | | T | | | | T | | | | / | | | 166-259/303-429 |
| Mt 83962 | / | / | / | | | | | | | | | | | C | | | 172-294/364-441 |
| Mt 77609 | / | / | / | / | / | / | / | / | / | / | / | / | / | / | A | T | 357-426 |
| Mt 79737 | / | / | / | / | / | / | / | / | / | / | / | / | / | / | | | 323-434 |

@ = NEW POLYMORPHISM POSITION

* = BASE CHANGE DIFFERENT FROM THAT REPORTED IN THE LITERATURE

/ = UNSEQUENCED REGION

SEQUENCING DNA; A MODIFICATION OF THE POLYMERASE CHAIN REACTION

SUMMARY OF INVENTION

The direct dideoxy sequencing of DNA which has been amplified by the polymerase chain reaction (PCR) is generally difficult and labor intensive because the complementary strand may displace the sequencing primer from the template strand. This problem has been eliminated by the use of a biolinylated primer and a primer which has not undergone biotinylation. This process facilitates separation of the DNA strands following the polymerase chain reaction process. The biotinylation/PCR product is then exposed to a support which will selectively bind the biotinylated strand. The non-biotinylated strand may then be removed from the mixture.

BACKGROUND OF THE INVENTION

The analysis of DNA has generated many advances in understanding and diagnosis of inherited disorders and pathogen-mediated diseases. (Caskey, *Science* 236, 1223–1229, (1987); Holt, *Nature* 331, 717–719.) Methods of DNA analysis have also been employed to quantify the level of genetic variation in populations, and have been applied to the forensic identification of individuals. (Jeffries, *Nature* 318,577–579, Higuchi, *Nature* 332, 543–546 (1988).) In many cases, DNA analysis such as restriction length polymorphism is insufficient and nucleotide sequence analysis is required. However, most DNA samples are too small and contain insufficient DNA to permit direct DNA sequencing. Recently, a method for rapidly amplifying microgram quantities of DNA from defined regions was developed. (Saki, *Science* 230, 1350–1354, (1985).) The method, known as the polymerase chain reaction (PCR) can increase the number of copies of DNA for analysis by up to 10 million fold from a sample containing only a single DNA molecule. (Saki, *Science* 239, 487–491, (1988).) The polymerase chain reaction method is taught in U.S. Pat. No. 4,683,202, which is incorporated herein by reference.

Direct dideoxy sequencing of PCR amplified DNA is generally difficult. This difficulty is caused by the physical nature of the PCR amplified DNA. After the PCR reaction, the product consists of short pieces of linear double stranded DNA (DS DNA), and contains unreacted primers and dideoxynucleotides. The unreacted primers cause two problems. The first is that these primers will prime sequencing reactions as well as the PCR reaction. Therefore, the sequencing primer must carry the only label in the sequencing reaction if any residual amplification primers are present, so that only the sequencing primer products are detectable. The second problem is that residual amplification primer will bind template sites, reducing the amount of template available to the sequencing primer.

Linear double stranded DNA is generally unsatisfactory as a template for dideoxy sequence reactions because the complementary strand can form many more hydrogen bonds than the sequencing primer. The complementary strand can displace the sequencing primer from a significant proportion of the template strands, greatly decreasing the amount of specific termination products formed in the subsequent sequencing reaction. The first method to overcome this problem utilized an M13 vector. The PCR amplified DNA was cloned into this vector to generate single strand DNA (SS DNA) for sequencing. (Scharf, *Science* 233, 1076–1078, (1986).) The results from M13 sequencing reactions are generally excellent, but cloning and processing the M13 virus requires several days. Recently, several alternative methods have been described in order to decrease the time required for obtaining sequence information following PCR.

The "triple primer method" described by Wrischnick et. al. provides for the removal of unreacted PCR primers by the use of a centrifugal filtration device. (Wrischnick et. al., *Nucleic Acid Research* 15 No. 2, 529–541 (1987).) The retained linear DS DNA is denatured by heat and sequenced with a nested third primer. The sequencing primer is required to be 5' end labeled to distinguish its chain termination products from those produced by residual amplification primers. This method has proven to be difficult since both the sequencing template and its complement are present, resulting in the loss of many template molecules by the re-annealing of the two PCR product strands.

Attempts to improve this method by the addition of a "blocking primer" to the triple primer method were unsuccessful. The "blocking" primer employed was a 50mer nucleotide complementary to the non-template strand. The blocker was designed to prevent the non-template strand from re-annealing to the template strand. A series of four 20mer primers complementary to the template were tried, the first ended 40 bases from the 3' end of the blocker, the second ended 9 bases from the 3' end of the blocker, the third primer overlapped the blocker by five bases, and the fourth completely overlapped the blocker.

Another possible method to prepare single stranded DNA from the PCR amplified DNA for sequencing involves separation of the PCR DNA into single strands by denaturing gel electrophoresis. Strand separation should be quite effective in producing high quality sequencing templates from DNA regions with sufficient strand bias. However, many DNA fragments do not contain the level of strand bias required to form separate single strands by denaturing gel electrophoresis by the method of Maniatis. (Maniatis, *Molecular Cloning Laboratory Manual*.) These DNA regions could not be sequenced by this method. The time needed to perform the strand separation electrophoresis and extraction of the strands, as well as the losses of DNA incurred during the extraction process was unacceptable long.

Another method suggested to avoid the strand bias problem would employ two rounds of PCR. Standard PCR amplification would be performed and the product purified by non-denaturing gel electrophoresis. The band of interest would be extracted and that DNA subjected to a second round of PCR in the presence of only one of the extension primers. Only one strand could be copied, primed by the single available primer. The final product should contain both double stranded DNA as well as single stranded DNA. The excess single stranded DNA would be available as a sequencing template. This double PCR method would require the time for gel electrophoresis/DNA extraction, as well as a second PCR reaction. A modified version of this method would limit the concentration of one amplification primer. As the PCR reaction progressed, the limited primer supply would be exhausted, so that only strands produced by the non-limited primer would continue to accumulate. This modification would eliminate the necessity for gel electrophoresis and a second round of PCR. When this method was employed it was not possible to obtain detectable quantities of SS DNA.

Stoflet et. al. introduced a method which utilizes a phage T7 promoter incorporated into one of the amplification primers. (Stoflet et. al., *Science* 239, 491–494, (1988).) Their method is known as genomic amplification with transcript sequencing (GAWTS). Following PCR, the product DNA contains a T7 promoter on one strand. This strand is transcribed by a promoter specific RNA polymerase, producing SS RNA. The RNA transcript is then sequenced using reverse transcriptase and a labeled third primer. Besides the sequence of interest, the amplified and transcribed product contains sequences from other genomic regions which cross-hybridize to the PCR primers. To avoid sequencing these contaminating regions, the reverse transcriptase primer should be complimentary to a region removed from the site of the amplification primer. This sequencing primer is also required to contain the only available label.

DESCRIPTION OF THE FIGURES

FIG. 4 shows alignment of base polymorphisms of Mt DNA sequenced by the method described in FIG. 3. Plasmids pCJK, PBHK, pLKK, PCDK were furnished by Barry Greenberg and Sugino. Mt DNA samples were obtained from donated platelets. Platelets were prepared using the method of Tapper. (Tapper, Van Ettan and Clayton, *Meth. Enz.* 97, 426–434, (1983).)

DESCRIPTION OF THE INVENTION

Figure 1A:
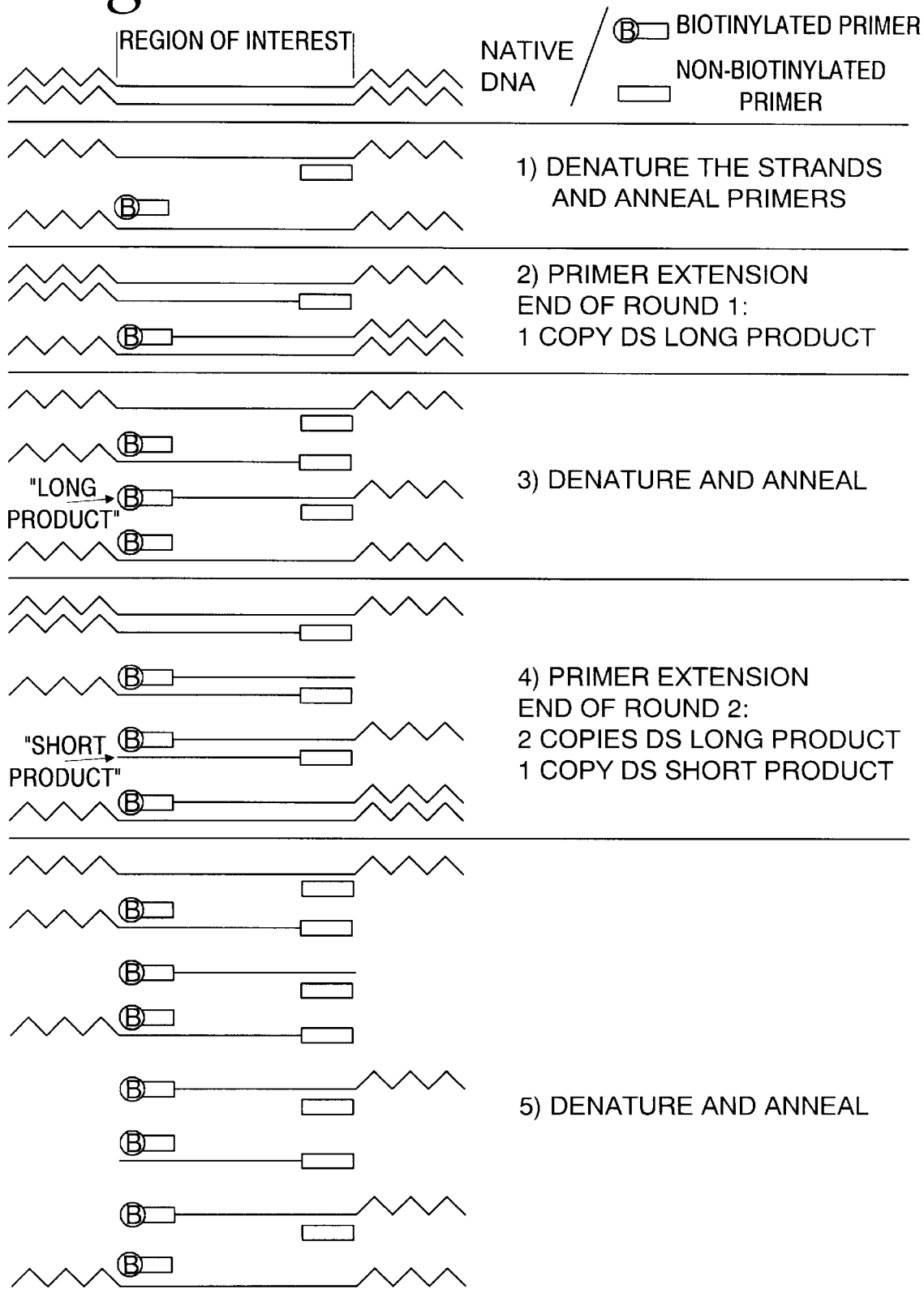
FIG. 1 is a diagram of the method which results in generation of single stranded DNA.

It is the purpose of this invention to provide a method to reliably produce single standard DNA, for example, for use in DNA sequencing that would be less time-consuming and that would provide a reliable means of sequencing DNA for analysis.

It is a further object of this invention to provide a more cost-effective method of sequencing DNA.

This invention provides a method for sequencing DNA based on the polymerase chain reaction (PCR) that is simplier to execute and faster than previously described methods. The primary inventive step is the biotinylation of one of the two extension primers used in the polymerase chain reaction amplification. One primer should be biotinylated. The primer was biotinylated on the 5' end in the examples. Upon completion of the PCR amplification step, the DNA product consists of double stranded DNA which has only one biotinylated strand. This PCR reaction product is then exposed to a substance which will selectively bind the biotinylated strand of DNA. The complementary strands are denatured and the non-biotinylated strand is then collected free from the bound biotinylated strand. The single stranded DNA free of it's complement strand can then undergo DNA sequencing. Alternatively, DNA may be amplified with a biotinylated primer and with a non-biotinylated primer in the presence of dideoxy-nucleotides which would constitute a DNA sequencing reaction. The product would then be exposed to a support which binds the biotin moiety. Denaturation of the two strands may then be accomplished. The non-biotinylated DNA would then be collected in accord with methods used to collect non-sequenced PCR amplified DNA. The examples provided are not to be considered as limitations, but merely as illustrations of the method claimed herein. Many variations in the method would be obvious to one of ordinary skill in the art.

In one instance, following the biotinylation primer/PCR process the PCR reaction product containing double stranded DNA having one biotinylated strand was treated in the following manner: an equal volume of streptavidin agarose was added to the reacted PCR mix and held at 37° for 30 minutes. The incubated mixture was then placed on a Sephadex G-50 spin column. The unreacted reagents were removed by two washes with 10 mM Tris-HCl (pH 7.4), 1mM EDTA (TE). Unlabeled SS DNA was eluted from the bound biotinylated strand by two sequential additions of 0.1N NaOH followed by centrifugation to increase recovery. The elutant was neutralized with ammonium acetate and recovered by ethanol precipitation. The resultant pellet was dissolved in TE. The single stranded DNA product is immediately available for use as template in dideoxy sequencing.

The interaction between streptavidin and biotin is highly specific and once formed is very difficult to dissociate. There is no requirement for the use of a labeled sequencing primer as the unreacted biotinylated primer is removed by the combination of streptavidin agarose and two washes through Sephadex G-50. This step alone represents a significant improvement over techniques which require radiolabeled primer for sequence visualization. Radiolabeled primers have short stabilities and provide only a single label for each strand generated by dideoxy termination.

As an alternative, a solution of 50% guanidine isothiocyanate/formamide could be employed to remove the streptavidin bound biotinylated/PCR processed DNA for use in dideoxy sequencing according to the method of Delius. (Delius, *Nucleic Acid Research* 13, 5457–5469, (1985).)

Currently two simultaneous PCR amplifications are performed for each region to be sequenced, with the forward primer biotinylated in one reaction, and the reverse primer biotinylated in the second. Magnetic beads have also been used. However, they have a lower affinity for biotin and are more expensive to use than streptavidin-agarose beads.

EXAMPLE I

Figure 1C:
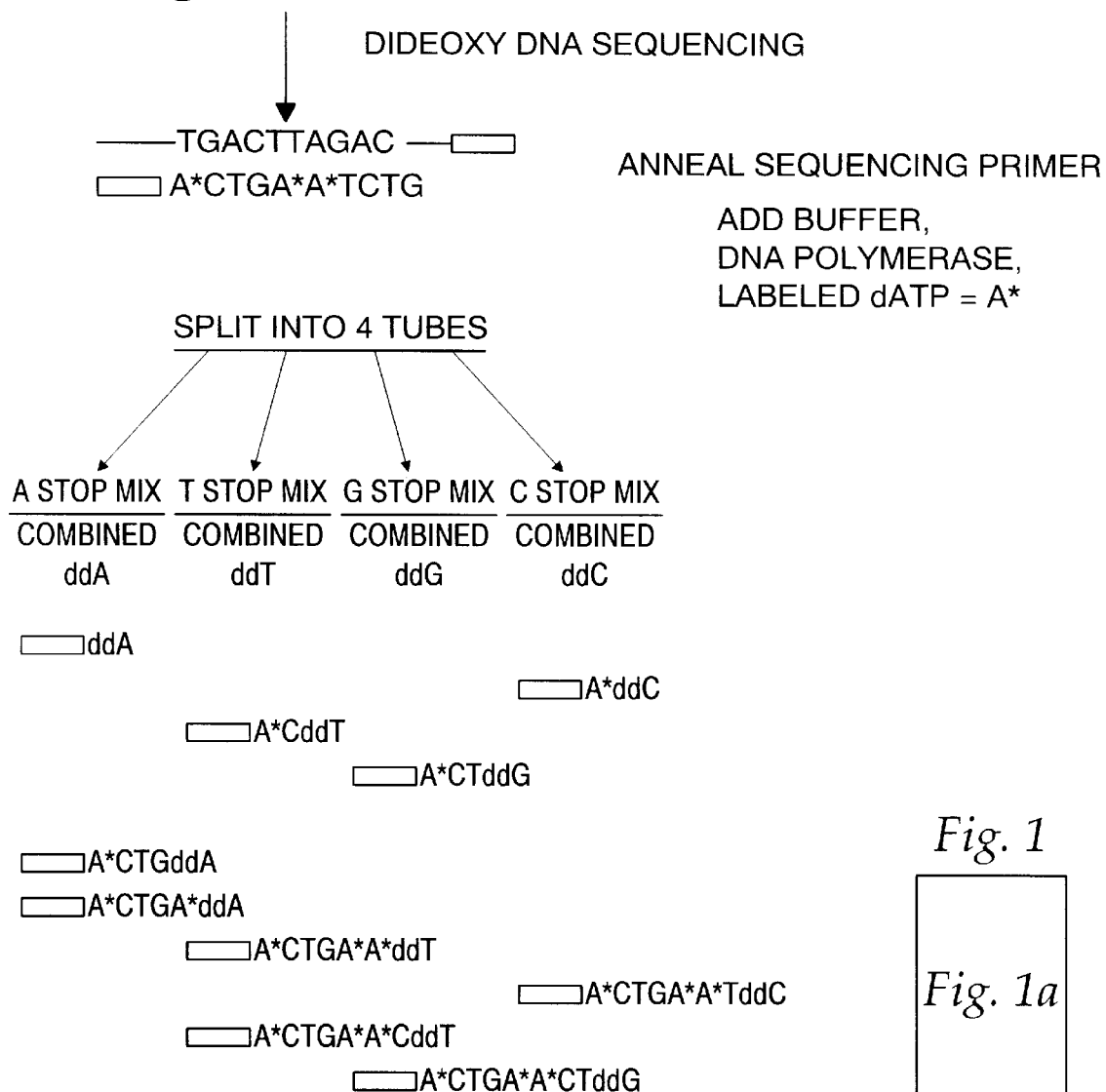

Single stranded DNA was generated as follows. An equal volume of streptavidin-agarose beads (Bethesda Research Labs) was added to the biotinylated/PCR crude product and held at 37° C. for 30 min with occasional shaking to resuspend the beads. (The streptavidin-agarose was washed 5× in TE and resuspended in enough buffer so that it could be easily pipetted.) The PCR-streptavidin-agarose mixture was pipetted onto a Sephadex G-50 spin column (Boerhinger) and washed twice with 0.5 ml TE followed by centrifugation at 1,000×g for 5 min. 0.1 ml of 0.1 N NaOH was added to the column to denature the DNA strands. After 6 minutes the column was spun at 1,000×g for 5 min. The NaOH denaturation step was performed two times. 0.2 ml of 5M ammonium acetate (pH 5.4) was added to the column, followed by centrifugation. Two volumes of ethanol were added to the recovered eluent, and held at −20° C. for 30 min. Single strands DNA was recovered by centrifugation for 20 min at 12,000×g. The resulting pellet was washed once in 70% ethanol and dried with vacuum centrifugation. The pellet was redissolved in 20 ul of TE buffer. The quantity of SS DNA was estimated by comparison of fluorescence of SS DNA to that of X174 marker in an ethidium stained agarose gel. Generally, 1.5 ul of the SS DNA solution provided sufficient template for dideoxy sequencing using Sequenase. (See FIG. 1.)

EXAMPLE II

Figure 2:
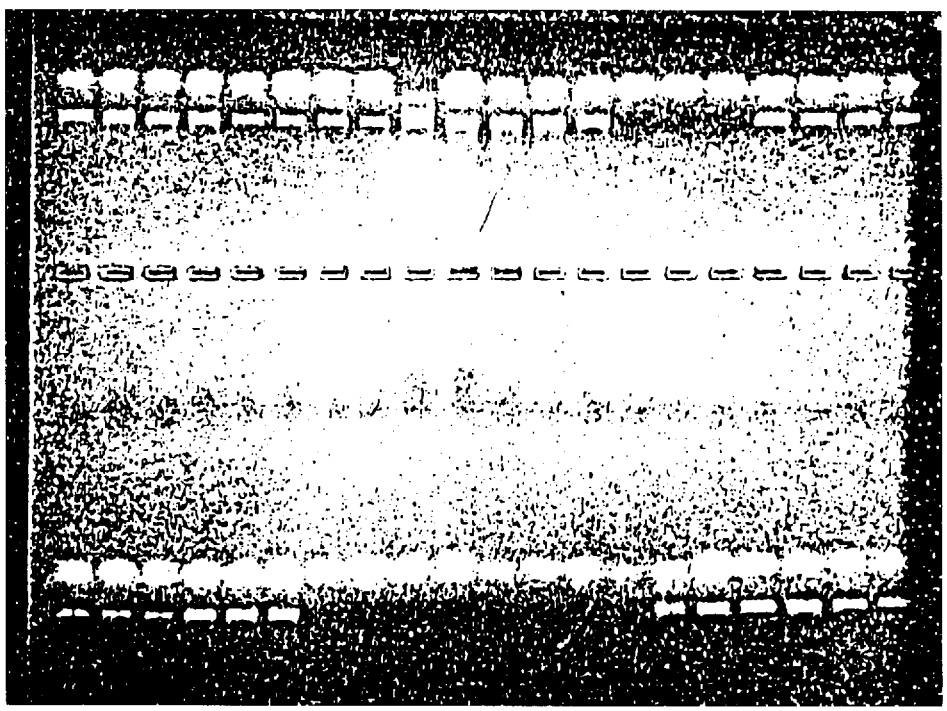
FIG. 2 is a photograph of the amplified DNA obtained in example II.

PCR was performed with Taq polymerase (Cetus) for 30 cycles by hand or using a Perkin-Elmer Cetus Thermal Cycler to amplify mitochondrial DNA lying between nucleotide positions 110 and 469. A cycle was defined as 1 minute at 90° C., 2 min at 54° C., and 3 min at 72° C. The PCR was carried out in a volume of 200 ul in the presence of 50 mM KC1, 10 mM Tris-HC1 (pH 8.3), 1.5 mM MgCl, 0.01% gelatin, 1 uM of a biotinylated primer (prepared by Clonetech) and 1 uM of non-biotinylated primer, 200 uM each DNTP, and 0.1 pg to 5 ng of target DNA. The primers were complementary to the Mitochondrial (Mt) DNA positions 90–109 (primer #10) and 489–470 (primer #12) (Anderson et. al., Nature 290, 457–465, (1981).). Each primer was synthesized both with and without biotin. PCR was performed twice on each sample for sequence analysis; one reaction with biotinylated #10 and unbiotinylated #12, the second reaction with unbiotinylated #10 and biotinylated #12. Amplification was verified by electrophoresis of 2.5% of the PCR product in a 1.5% agarose gel, along with 0.5 ug of X174 Hae III DNA fragments. After the gel was stained with ethidium bromide, the amount of product was estimated based on comparison between the UV fluorescence of the amplified DNA band and the size marker bands. (See FIG. 2.)

EXAMPLE III

The template for dideoxy sequencing was made as described in Example 2. Sequence reactions were performed with modified a T7 DNA polymerase (Sequenase US Biochemical) using the reagents and conditions supplied by the manufacturer. Because the template DNA was relatively short, the primer-template-enzyme-label mix was added to the premixed dNTP-ddNTP's so that the proximal region of the template would be sequenced. Electrophoretic separation was performed in an 8% bis-acrylamide gel (See FIG. 3).

EXAMPLE IV

Biotinylation of the primer

Nucleic acid primer sequence of the structure GCGAGACGCT GGAGCCGGAG (primer #10) was synthesized with an amino modifier, AminoModifer I (AMI) obtained from Clonetech Laboratories to produce a modified primer using a DNA synthesizer. The modified primer was removed from the column by elution with concentrated ammonium hydroxide. The modified primer was then deprotected by treatment with 80:20 acetic acid:water for one hour at room temperature.

Biotinylation of the modified primer was carried out in the following manner: to 0.1 uM deprotected modified primer in 800 ul of 100 mM sodium bicarbonate (pH 9) was added 200 ul of a 10 mg/ml solution of biotin (Biotin-X-NHS ester, where x is a 6-aminocaproic acid spacer, a product of Clonetech) in N,N dimethylformamide. The solution was allowed to stand overnight. The biotinylated product was used in the process of Example 2.

Results

Figure 3:
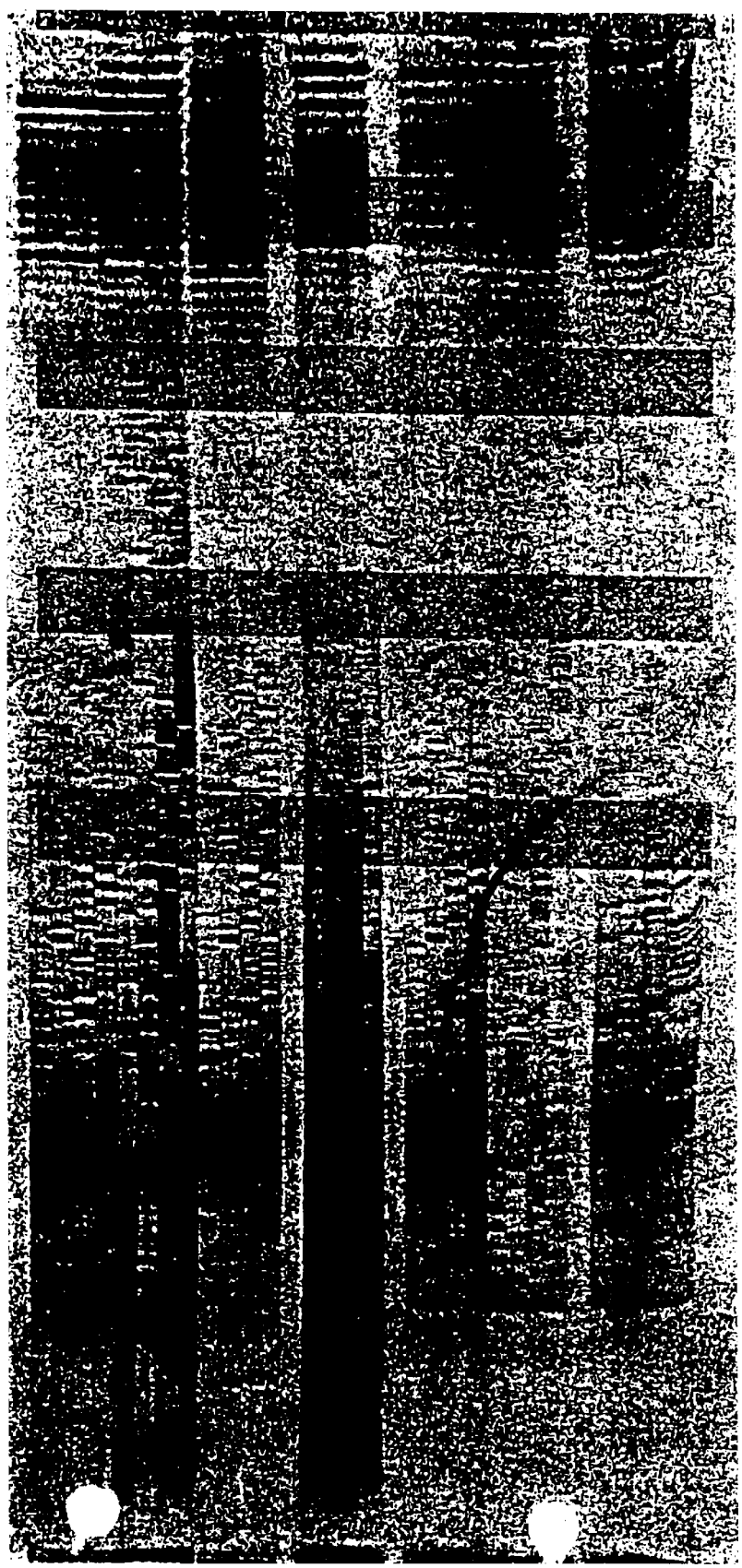
FIG. 3 is an autoradiograph of sequences obtained by the biotinylation/PCR primer method. The template for dideoxy sequencing was made as described in FIG. 2. Sequence reactions were performed with modified a T7 DNA polymerase (Sequenase from US Biochemical) using the reagents and conditions supplied by the manufacturer. Because the template DNA was relatively short, the primer-template-enzyme-label mix was added to the premixed dNTP-ddNTP's so that the proximal region of the template would be sequenced. Electrophoretic separation was performed in an 8% Bis-acrylamide gel. Arrow *(s) indicate sequence polymorphisms.

The first region chosen for sequencing using the biotinylated primer PCR method was a section of the mitochondrial D-loop lying between the nucleotide positions 110 and 469. (Anderson et. al. Nature 290, 457–465, (1981).) Mitochondrial D-loop sequences are highly polymorphic between individuals. (Greenberg, Gene 21, 33–49, (1983).) The region between 110 and 469 has been described as hypervariable compared to average D-loop variability. (Aquadro et. al., Genetics 103, 287–312, (1983).) Amplification primers and PCR conditions were as described in Example 2. To determine the fidelity of the biotinylated primer PCR method, D-loop clones for which sequences had previously been reported were sequenced. A total of 783 nucleotides from four clones was determined. (FIG. 3.) All previously documentated polymorphisms in the regions sequenced with the single exception of clone pCDK position 186, which we recorded as a G to T transversion were verified. (Greenberg had reported this as a G to A transition.)

Sequences were also determined for 751 nucleotides from five individuals with the biotinylated primer PCR method. A total of 13 differences were discovered in comparison to the sequence published by Anderson. (FIG. 4.) Four of these changes occured at positions where polymorphism had not been previously noted.

There is a high level of agreement for the cloned Mitochondrial DNA sequences obtained using the biotinylated primer PCR method and the original M13 sequencing. The single divergence between the results of the two methods could possibly be an artifact caused by passage in the cloning vector. Sixty-nine percent of the changes reported for newly sequenced individuals occur at positions previously identified as polymorphic, again indicating a high level of sequencing fidelity.

The entire biotinylated primer PCR method including: PCR amplification, strand separation, dideoxy reaction, and gel manipulations to the point of exposing the autoradiogram, can easily be performed on twelve samples in a normal working day. There are now several methods available for rapid and direct sequencing of PCR amplified DNA. The biotinylated primer PCR method allows the user to avoid the difficulty of sequencing a linear DS DNA template and eliminates the need for a third polymerase system.

The technique of biotinylated primer PCR should have applications in both fields of research and clinical medicine. In the case of a gene for which the sequence of one allele is known, the rapid sequencing of the same gene from individuals with defective function could lead to elucidation of the responsible mutation. Possible clinical applications include direct carrier testing, prenatal detection of genetic mutation, diagnosis of infectious diseases, and forensic identification. The single stranded DNA could be used for purposes such as for generation of probes.

We claim:

1. A process for preparing DNA amplified by a polymerase chain reaction which comprises:

binding biotin to an oligonucleotide to produce a biotinylated oligonucleotide primer for use in a polymerase chain reaction, amplifying a nucleic acid by a polymerase chain reaction by use of said biotinylated oligonucleotide primer and a second non-biotinylated oligonucleotide primer, reacting the thus produced amplified double-stranded DNA with a solid support to bind said amplified DNA to said solid support through said biotin, denaturing the DNA to separate from said double-stranded DNA the biotin-free single DNA strand which does not have biotin bound thereto, and recovering said biotin-free DNA strand.

2. A process for the preparation of single-stranded nucleic acid which comprises:
   i) conducting a polymerase chain reaction amplification of a nucleic acid template by utilizing a first primer which is an oligonucleotide having biotin bound thereto and a second primer which is an oligonucleotide free of biotin to produce a double-stranded nucleic acid product having said first primer incorporated into only one of the two strands,
   ii) contacting said double-stranded nucleic acid product with a solid support including a moiety capable of specifically binding to biotin whereby said double-stranded nucleic acid product binds to said solid support;
   iii) exposing said solid support to a buffer capable of separating the strands of said double-stranded nucleic acid product without disrupting the binding of said biotin to said solid support; and
   iv) separating said buffer containing single-stranded nucleic acid free of biotin from said solid support having the biotinylated strand bound thereto.

3. A process for the preparation of single-stranded nucleic acid that comprises:
   i) selecting a solid support that is derivatized with a moiety that specifically binds to biotin;
   ii) covalently modifying an oligonucleotide primer with biotin; said
   iii) utilizing said biotin-modified oligonucleotide and a second oligonucleotide free of biotin as the primers in a polymerase chain reaction amplification of a nucleic acid template;
   iv) contacting the products of the polymerase chain reaction of step (iii) with said solid support;
   v) purifying the double-stranded product incorporating the biotin-modified oligonucleotide of step (ii) by washing said polymerase chain reaction products bound to said solid support with a buffer that does not denature complementary nucleic acid strands;
   vi) separating the complementary nucleic acid strands by exposing the solid support, with the double-stranded polymerase chain reaction product attached, to a buffer which will denature complementary nucleic acid strands, but which will not disrupt the specific binding of the biotin-binding moiety to biotin;
   vii) separating the solid support with the attached, biotin-labelled denatured polymerase chain reaction product from the denaturing buffer; and
   viii) collecting the single-stranded polymerase chain reaction product from the buffer.

4. A process for sequencing a nucleic acid amplified by a polymerase chain reaction which comprises:
   i) binding biotin to an oligonucleotide to produce a biotinylated oligonucleotide primer for use in a polymerase chain reaction,
   ii) amplifying a nucleic acid by a polymerase chain reaction by use of said biotinylated oligonucleotide primer and a second non-biotinylated oligonucleotide primer,
   iii) reacting the thus produced double-stranded DNA with a solid support to bind said double-stranded DNA to said solid support through said biotin,
   iv) denaturing the double-stranded DNA to separate from said double-stranded DNA the biotin-free single DNA strand which does not have biotin bound thereto,
   v) recovering said biotin-free DNA strand, and
   vi) determining the sequence of nucleotides comprising said biotin-free DNA strand.

5. A process for sequencing a nucleic acid that comprises:
   i) conducting a polymerase chain reaction amplification of a nucleic acid template by utilizing a first primer which is an oligonucleotide having biotin bound thereto and a second primer which is an oligonucleotide free of biotin to produce a double-stranded nucleic acid product having said first primer incorporated into only one of the two strands,
   ii) contacting said double-stranded nucleic acid product with a solid support including a moiety that specifically binds to biotin thereby binding said double-stranded nucleic acid product to said solid support;
   iii) exposing said solid support to a buffer capable of separating the strands of said double-stranded nucleic acid product without disrupting the binding of said biotin to said solid support;
   iv) separating said buffer containing single-stranded nucleic acid free of biotin from said solid support having the biotinylated strand bound thereto; and
   v) determining the sequence of nucleotides comprising the single-stranded nucleic acid in said buffer.

6. A process for sequencing a single-stranded nucleic acid that comprises:
   i) selecting a solid support that is derivatized with a moiety capable of binding to biotin;
   ii) covalently modifying an oligonucleotide primer with biotin;
   iii) utilizing said biotin-modified oligonucleotide with a second oligonucleotide free of biotin as the primers in a polymerase chain reaction amplification of a nucleic acid template;
   iv) contacting the products of the polymerase chain reaction of step (iii) with said solid support;
   v) purifying the double-stranded product incorporating the biotin-modified oligonucleotide of step (ii) by washing said polymerase chain reaction products bound to said solid support with a buffer that does not denature complementary nucleic acid strands;
   vi) separating the complementary nucleic acid strands by exposing the solid support, with the double-stranded polymerase chain reaction product attached, to a buffer which will denature complementary nucleic acid strands, but which will not disrupt the specific binding of the biotin-binding moiety to biotin;
   vii) separating the solid support with the attached, biotin-labelled denatured polymerase chain reaction product from the denaturing buffer;
   viii) collecting the single-stranded polymerase chain reaction product from the buffer; and
   ix) determining the sequence of nucleotides comprising said biotin-free DNA strand.

7. A process for sequencing a nucleic acid that comprises:
   i) conducting a polymerase chain reaction amplification of a nucleic acid template by utilizing a first primer which is an oligonucleotide having biotin bound thereto and a second primer which is an oligonucleotide free of biotin to produce a double-stranded DNA product having said first primer incorporated into only one of the two strands, ii) contacting said double-stranded DNA with a solid support including a moiety that specifically binds to biotin whereby said double-stranded DNA binds to said solid support;

iii) exposing said solid support to a buffer capable of separating the strands of said double-stranded DNA without disrupting the binding of said biotin to said solid support;

iv) separating said buffer thus containing single-stranded DNA free of biotin from said solid support having the biotinylated strand of DNA bound thereto; and v) determining the sequence of nucleotides comprising the single-stranded DNA in said buffer.

* * * * *